United States Patent [19]

Clubley et al.

[11] 4,370,281

[45] Jan. 25, 1983

[54] TRIARYL PHOSPHATES

[75] Inventors: Brian G. Clubley, Wilmslow; Thomas G. Hyde, Sale; John F. E. Keenan, Cheadle Hulme, all of England

[73] Assignee: Ciba-Geigy AG, Basel, Switzerland

[21] Appl. No.: 306,934

[22] Filed: Sep. 29, 1981

Related U.S. Application Data

[63] Continuation-in-part of Ser. No. 57,249, Jul. 13, 1979, abandoned.

[30] Foreign Application Priority Data

Jul. 21, 1978 [GB] United Kingdom ............... 30742/78

[51] Int. Cl.$^3$ ............................................... C07F 9/09
[52] U.S. Cl. ..................................... 260/966; 260/982
[58] Field of Search .......................................... 260/966

[56] References Cited

U.S. PATENT DOCUMENTS 3,028,410 4/1962 Zimmer, Jr., et al. ............... 260/920
3,363,033 1/1968 Witt ..................................... 260/982
3,919,158 11/1975 Randell et al. ....................... 260/966

FOREIGN PATENT DOCUMENTS 2159264 9/1973 France .
2027712 2/1980 United Kingdom .

*Primary Examiner*—Anton H. Sutto
*Attorney, Agent, or Firm*—Wenderoth, Lind & Ponack

[57] ABSTRACT

The invention provides triaryl phosphates of the general formula

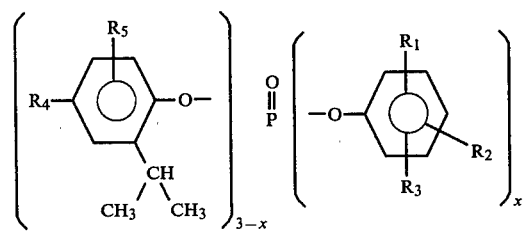

wherein x is 1 or 2, $R_1$ is hydrogen, $R_2$ and $R_3$ are the same or different and represent hydrogen, t-butyl or isopropyl, $R_4$ is hydrogen or an isopropyl group and $R_5$ is an isopropyl group, with the proviso that at least one of the aryl radicals is a di-isopropylphenyl radical, but not more than two of the three aryl groups are identical.

4 Claims, No Drawings

TRIARYL PHOSPHATES

This application is a continuation-in-part of Ser. No. 057,249, filed July 13, 1979, now abandoned.

The present invention relates to novel triaryl phosphate mixtures and their use as flame retardant functional fluids, e.g. for hydraulic or electrical use, and as flame retardant additives for polymers.

Accordingly, the present invention provides novel mixtures of triaryl phosphates having the overall general formula I

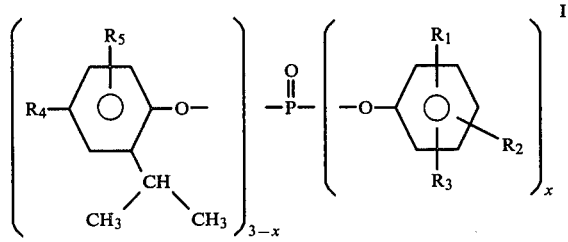

wherein x is 1 or 2, $R_1$ is hydrogen, $R_2$ and $R_3$ are the same or different and represent hydrogen, t-butyl or isopropyl, $R_4$ is hydrogen or an isopropyl group and $R_5$ is an isopropyl group with the proviso that at least one of the aryl radicals is a di-isopropylphenyl radical, but not more than two of the three aryl groups are identical.

Although radicals $R_2$ and $R_3$ may occupy any positions on the ring, they preferably occupy the 2,4 or 6 position. $R_5$ may occupy the 5 or 6 position on the ring, but preferably the 6 position.

Preferably at least one of $R_2$ and $R_3$ is isopropyl.

The phosphate esters described in the invention may be prepared by known methods. For example, the appropriate phenols may be reacted with a phosphorylating agent. The phosphorylating agent may be, for example, phosphorus oxychloride or phosphorus pentachloride. The phosphorylation reaction may be performed in the presence of a catalyst, such as aluminium chloride or magnesium chloride, or in the presence of a base, such as pyridine. The phosphates may also be prepared by reacting the sodium salt of the phenol with the phosphorylating agent or by oxidising the corresponding phosphorous acid esters by known procedures.

The isopropylated phenols used to prepare the phosphate esters of the invention may be prepared by alkylating phenol with a suitable alkylating agent, such as propylene, at an elevated temperature, e.g. 140° C., in the presence of a Friedel-Crafts catalyst or an acid earth catalyst. The alkylation reaction should be carried out for a long enough time for a major proportion of the phenol to be substituted by at least two isopropyl groups. For instance, the reaction may be continued until no more alkylating agent will react with the phenol. The resulting isopropylated phenol product can then be reacted in toto with the phosphorylating agent, or if desired, in admixture with phenol or other alkyl phenols.

The triaryl phosphates of the invention can be used as flame retardant additives for thermoplastic or thermosetting polymers and, where the compounds are liquid, as flame retardant functional fluids.

Examples of the polymers which may be made flame retardant by addition of compounds of the invention are: polystyrene, polyethylene, polypropylene, polyvinyl acetate, polyacrylonitrile, cellulose, polyesters, polycarbonates, rubbers, phenol formaldehyde resins, epoxy resins, polyester resins, amino formaldehyde resins, polyamides or copolymers and poly blends of the afore mentioned polymers and resins. Examples of poly blends are polystyrene/poly-2,6-dimethyl-1,4-phenylene oxide, especially high impact polystyrene/poly 2,6-dimethyl-1,4-phenylene oxide. Certain of the products of the invention which are liquids can be used to plasticise PVC or as flame retardant hydraulic fluids or flame retardant fluids for electrical use, e.g. for transformers or capacitors.

The amounts of compound I which are incorporated into a polymer when the compounds are used as flame retardant additives or plasticisers are from 1 to 150 parts, preferably 2-80 parts, more preferably 3-50 and most preferably 5-25 parts per hundred parts of polymer. The amount of phosphate used will depend on the type of polymer, the properties required and the amount and type of other ingredients which may be present.

The phosphates of the invention may also be used in conjunction with an oligomer of the general formula II

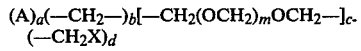

wherein A is at least one aromatic hydrocarbon or heterocyclic residue, X is a leaving group, a is 2 to 20 but equals b+c+1, b is 0 to 19, c is 0 to 19, d is 0 to 20 and m is 0 to 10, preferably 0-5, most preferably 0, there being at least two (—$CH_2X$) groups per molecule, the group (—$CH_2OCH_2$—) counting as (—$CH_2X$) for this purpose, when m=0, and the group (—$CH_2O$) counting as (—$CH_2X$) when m≧1.

It should be noted that the values of a, b, c, d and n are average values for the average molecule of formula II.

Leaving group X in formula II is halogen, —OH, —SH, —$NH_2$, —$CO_2H$, —$PO_3H_2$, $OB(OH)_2$ and their derivatives, for example —$OR^1$, —$SR^1$, —$NHR^1$, —$NR^1R^2$, —$OB(OR^1)(OR^2)$. Non-limiting examples of such derivatives and other X groups may be represented by the general formulae

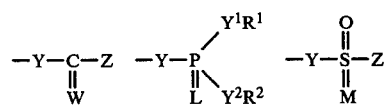

where
$Y$, $Y^1$ and $Y^2$ are, independently, —O—, —NH—,

—S—, or are absent, but preferably are —O— or —S—;
Z is H, $R^1$, $OR^1$, —$SR^1$, $NH_2$, $NHR^1$, $NR^1R^2$ or a direct bond linking

back to R or to a $CH_2$ attached to R but preferably is H or $R^1$;
W is O, S, NH or $NR^1$, but preferably is O or S;
L is O, S or is absent, but preferably is O;

M is O or is absent, but preferably is O;
and wherein R¹ represents a straight or branched The group —CH₂OCH₂— being counted as a —CH₂X group.

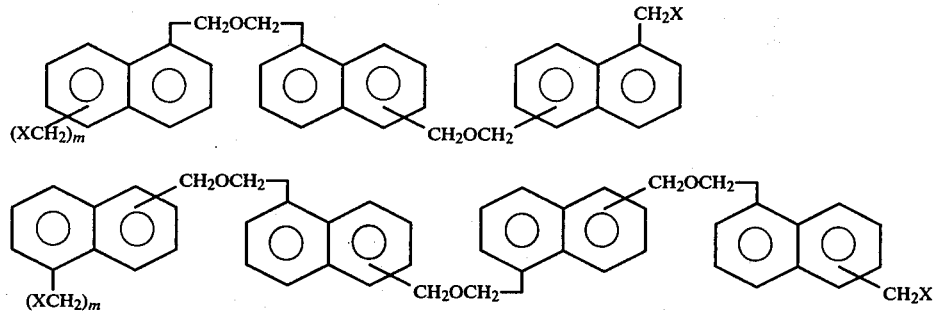

chain alkyl having 1 to 12 carbon atoms, preferably 1 to 4, but most preferably 1, alkenyl or alkynyl having 2 to 12 carbon atoms, preferably 2 to 4, cycloalkyl or cycloalkenyl having 5 to 12, preferably 6 carbon atoms, aralkyl, aralkenyl or alkaryl having 7 to 12 carbon atoms, preferably benzyl or naphthyl methyl or aryl having 6 to 15, preferably 6 to 12 carbon atoms, most preferably benzyl or naphthyl methyl. R¹ may be optionally substituted by one or more halogen, hydroxy, epoxy, nitrile, amine, amide, ether, carboxyl or ester groups or combinations thereof, but is preferably unsubstituted. R² has the same significance as R¹ and may be the same or different. The leaving group may also be a salt of an acidic or basic X group.

However, of the non-limiting examples, compounds of formula I where X=OH or a derivative of this group are preferred.

Examples of aromatic residues A are benzene, naphthalene, furan, anthracene, biphenyl and diphenyl ether. The aromatic residue A may be unsubstituted or substituted by one or two substituents. It is preferably unsubstituted, but if it is substituted it preferably carries only one substituent. Suitable substituents include halogen, alkyl groups with 1 to 4 carbon atoms, haloalkyl groups with 2 to 4 carbon atoms, and the group OR³ where R³ is hydrogen, alkyl with 1 to 4 carbon atoms or acyl with 1 to 4 carbon atoms.

The compounds represented by formula II are mixtures of oligomers with a range of molecular weights. The residues A are linked by (—CH₂—) or [—CH₂(OCH₂)$_m$OCH₂—] groups, these two linking groups being connected only to a residue A and not to each other. The groups (—CH₂X) are connected to a residue A.

Preferably greater than 50 mol % of residues A are derived from naphthalene; most preferably more than 75 mol % of residues A are derived from naphthalene.

Oligomers which are preferred are those having a number average weight of 300 to 3500, more preferably those having a number average molecular weight of 350–1500, most preferably 400 to 1000. It is preferred that the naphthalene residues are linked by (—CH₂OCH₂—) and that these links should be attached to the positions 1,4; 1,5; 1,6; 1,7; 2,5; 2,6 or 2,7 on the naphthalene residue. It is most preferred that the links should be attached to the 1,4 or 1,5 positions on the naphthalene residue.

Non-limiting examples of particular oligomers of structure II are those linked by the group —CH₂OCH₂— and having two or more —CH₂X groups per molecule. Preferred structures which can be present as a component of the oligomer mixture are shown below.

Where m=0 or 1, and X=OH $$-O\overset{O}{\underset{\|}{C}}CH_3 \quad -OCH_2\text{—Ph} \quad \text{or} \quad -O\text{—Ph}$$

Specific Examples of oligomers which can be present as components of the oligomer mixture are listed in Table A:

TABLE A

| Molecular Weight | Aromatic hydrocarbon corresponding to Residue A | a | b | c | d | m | X |
|---|---|---|---|---|---|---|---|
| 440 | naphthalene | 2.75 | 0.59 | 1.20 | 1.10 | 0 | —OH |
| 385 | naphthalene | 2.42 | 0.07 | 1.32 | 0.82 | 0 | —OH |
| 540 | naphthalene | 3.44 | 0.44 | 2.00 | 0.39 | 0 | —OH |
| 760 | naphthalene | 4.82 | 0.61 | 3.21 | 0.11 | 0 | —OH |
| 890 460¹ | diphenyl ether | 3.78 | 1.20 | 1.57 | 0.84 | 3 | —OH |
| 615² | naphthalene | 2.82 | 0 | 4.45 | 2.05 | 0 | —OH |

¹Molecular Weight of oligomer/bis-HOCH₂—naphthalene mixture
²Molecular Weight of oligomer component The addition of such an oligomer is especially useful in thinner section polymer sheets, e.g. 1.5 mm. to provide polymer sheets which do not drip when burnt.

Examples of other ingredients which may be present in the compositions of the invention are: heat stabilisers, light stabilisers, UV absorbers, antioxidants fillers, pigments, lubricants, additives to improve mold release, fungicides, blowing agents, optical brightening agents, other fire retardant additives, processing aids, smoke suppressants, dyes, antioxidants, metal passivators/corrosion inhibitors, rust inhibitors, additives for improving hydrolytic stability, viscosity index improvers, extreme pressure/anti wear additives, pour point depressants, dispersants or detergents and anti foams.

The choice of these other ingredients will depend on whether the phosphates of the invention are used as functional fluids or as flame retardant additives to plastics.

Suitable other flame retardant additives include bromine-containing compounds such as pentabromo-diphenyl ether, decabromo-diphenyl ether and tetrabromo-bisphenol A.

When used as flame retardant additives, particularly in polystyrene/polyphenylene oxide blends, phosphates of the invention can give compositions with improved Heat Distortion Temperatures compared with known triaryl phosphate additives.

When used as functional fluids, phosphates of the invention show a smaller viscosity change and lower acid value change than known triaryl phosphate fluids, such as trixylyl phosphate.

The following Examples illustrate the invention.

EXAMPLE 1

658 parts of phenol and 40 parts Fulcat 22A catalyst were heated to 140° C. under nitrogen. The nitrogen was then replaced by propylene and propylene gas passed into the stirred reaction mixture at a rate of 1 liter/minute until no more would react. The isopropylated phenol product was then filtered off and was found to have the following composition:
4.9% di-isopropyl phenols
79.3% 2,4,6-tri-isopropyl phenol
15.8% 2,4,5-tri-isopropyl phenol 110 parts of the above phenol mixture, 76.8 parts of phosphorus oxychloride and 1 part of aluminium chloride were heated to 150° C. over 5 hours with stirring and then for a further 2 hours at 150° C. 99 parts of phenol were then added and the mixture heated to 200° C. over 3 hours followed by 3 hours at 200° C. The product was purified by distillation to give a colourless liquid, boiling point 180°–185° C./0.1 mm. Hg., viscosity at 25° C. = 640 c/s.

EXAMPLE 2

926 parts of phenolic mixture of composition

|  | % |
|---|---|
| phenol | 17.2 |
| 2-isopropylphenol | 32.3 |
| ¾-isopropylphenol | 7.2 |
| 2,6-di-isopropylphenol | 23.6 |
| 2,4 di-isopropylphenol | 7.7 |
| 2,5/3,5-di-isopropylphenol | 1.6 |
| 2,4,6-tri-isopropylphenol | 9.1 |
| 2,4,5-tri-isopropylphenol | 0.3 | were mixed with 2 parts of aluminium chloride and heated with stirring to 100° C. 307 parts of phosphorus oxychloride were then added over 2 hours, the temperature being gradually increased from 100° C. to 130° C. at the end of the addition. The reaction mixture was then heated to 200° C. over 2 hours and stirred at 200° C. for 1 hour.

The mixture was then de-gassed by stirring at 200° C. under water pump vacuum for 8 hours. The product was purified by vacuum distillation to yield 867 parts of a colourless liquid, boiling point 220°–240° C./0.5 mm Hg, viscosity at 40° C. = 132 c/s.

EXAMPLE 3

904 parts of a phenolic mixture of composition

|  | % |
|---|---|
| phenol | 13.4 |
| 2-isopropylphenol | 30.3 |
| ¾-isopropylphenol | 5.4 |
| 2,6 di-isopropylphenol | 30.0 |
| 2,4 di-isopropylphenol | 6.6 |
| 2,5/3,5-di-isopropylphenol | 1.4 |
| 1,4,6-tri-isopropylphenol | 11.3 |
| 2,4,5-tri-isopropylphenol | 0.3 | were mixed with 2 parts of aluminium chloride and heated with stirring to 100° C. 307 parts of phosphorus oxychloride were then added over 2 hours, the temperature being gradually increased from 100° C. to 130° C. at the end of the addition. The reaction mixture was then heated to 200° C. over 2 hours and stirred at 200° C. for 1 hour.

The mixture was then de-gassed by stirring at 200° C. under water pump vacuum for 8 hours. The product was purified by vacuum distillation to yield 881 parts of a colourless liquid, boiling point 220°–245° C./0.5 mmHg, viscosity at 40° = 188 c/s.

EXAMPLE 4

728 parts of a phenolic mixture of composition

|  | % |
|---|---|
| phenol | 0.3 |
| 2-isopropylphenol | 13.4 |
| ¾-isopropylphenol | 0.2 |
| 2,6 di-isopropylphenol | 56.5 |
| 2,4 di-isopropylphenol | 2.0 |
| 2,5/3,5 di-isopropylphenol | 0.7 |
| 2,4,6 tri-isopropylphenol | 24.4 |
| 2,4,5 tri-isopropylphenol | 0.2 | were mixed with 614 parts of phosphorus oxychloride and 8 parts of aluminium chloride. The mixture was heated with stirring to 160° C. over 5 hours. The mixture was then cooled to 75° C. and 1144 parts of a phenolic mixture of composition

|  | % |
|---|---|
| phenol | 26.8 |
| 2-isopropylphenol | 36.8 |
| ¾-isopropylphenol | 11.3 |
| 2,6 di-isopropylphenol | 8.0 |
| 2,4 di-isopropylphenol | 10.2 |
| 2,5/3,5 di-isopropylphenol | 1.9 |
| 2,4,6 tri-isopropylphenol | 3.9 |
| 2,4,5 tri-isopropylphenol | 0.6 | were added over 45 minutes at 75° to 90° C. The reaction mixture was then heated to 220° C. over 2 hours and stirred at 220° C. for 6 hours.

The mixture was then de-gassed by stirring at 220° C. under water pump vacuum for 3 hours.

The product was purified by vacuum distillation to yield 1708 parts of a colourless liquid, boiling point 204°–224° C./0.3 mm Hg, viscosity at 40° C. = 178 c/s.

EXAMPLE 5

1184 parts of a phenolic mixture of composition

|  | % |
|---|---|
| phenol | 0.1 |
| 2-isopropylphenol | 1.7 |
| ¾ isopropylphenol | 0.2 |
| 2,6 di-isopropylphenol | 63.8 |
| 2,4 di-isopropylphenol | 4.3 |
| 2,5/3,5 di-isopropylphenol | 1.5 |
| 2,4,6 tri-isopropylphenol | 25.5 |
| 2,4,5 tri-isopropylphenol | 0.5 | were mixed with 460.5 parts of phosphorus oxychloride and 6 parts of aluminium chloride. The mixture was heated with stirring to 200° C. over 6 hours and heating continued at 200° C. for a further 2 hours. The mixture was then cooled to 80° C. and 310 parts of phenol were added over 1 hour at 80° to 90° C. The reaction mixture was then heated to 240° C. over 5 hours and stirred at 240° C. for 4 hours.

The mixture was then de-gassed by stirring at 200° C. under water pump vacuum for 3 hours.

The product was purified by vacuum distillation to yield 1320 parts of a colourless liquid, boiling point 195°–210° C./0.3 mmHg, viscosity at 40° C.=1949 c/s.

EXAMPLE 6

The compositions shown in Table 1 were prepared by mixing 100 parts of a poly-2,6-dimethyl-1,4-phenylene oxide/polystyrene blend sold under the Trade Name Noryl 731 with 12 parts of phosphate and 1 part of phenolic novolak for 10–15 minutes at 240° C. followed by pressing at 245° C. to give a 3 mm sheet. The Heat Distortion Temperatures were then measured.

TABLE 1

| Example No. | Phosphate | Heat Distortion Temperature (°C.) |
|---|---|---|
| 6 | Product from Example 5 | 96 |
| A | Triphenylphosphate | 83 |

The results show a clear advantage of a phosphate of the present invention (Example 5) over Comparative Example A—triphenylphosphate.

EXAMPLE 7

The products of Examples 2 and 3 were tested as hydraulic fluids and compared with commercial trixylyl phosphate (TXP). The compounds were tested according to U.S. Federal Test Method STD No. 791 a, Method No. 5308.5. The following modifications were made: in paragraph 1.1 a temperature of 150° C. was used instead of 250° F. and in paragraph 5.2 a temperature of 40° C. was used instead of 100° F.

| Phosphate | High Viscosity TXP | Product of Example 2 | Product of Example 3 |
|---|---|---|---|
| Final Viscosity (at 40° C.) | 82.75 | 126.36 | 220.89 |
| Initial Viscosity (at 40° C.) | 75.57 | 117.80 | 210.65 |
| Change | 6.18 | 8.56 | 10.24 |
| % Change | 8.2% | 7.3% | 4.86% |
| Final Acid Value (mgKOH/g) | 0.59 | 0.24 | 0.39 |
| Initial Acid Value (mgKOH/g) | 0.11 | 0.04 | 0.07 |
| Change | +0.48 | +0.20 | +0.32 |

In all cases there was negligible corrosion of the metal speciments steel, copper, cadmium/steel, aluminium and magnesium.

The phosphates contained as additives, 0.2% of 2,6-di-tert-butyl-4-methyl phenol and 0.01% of benzotriazole.

Examination of the above results shows that the compounds of the invention have a lower percentage viscosity change and a lower acid value change than commercial TXP.

What we claim is:

1. Mixtures of triaryl phosphates of the overall general formula I

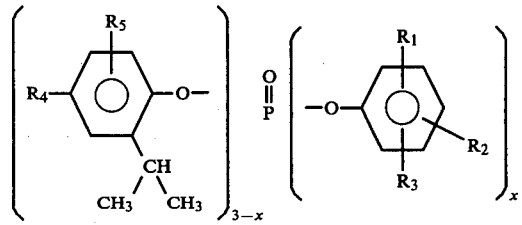

wherein x is 1 or 2, $R_1$ is hydrogen $R_2$ and $R_3$ are the same or different and represent hydrogen, t-butyl or isopropyl, $R_4$ is hydrogen or an isopropyl group and $R_5$ is an isopropyl group with the proviso that at least one of the aryl radicals is a di-isopropylphenyl radical, but not more than two of the three aryl groups are identical.

2. Mixtures of triaryl phosphates as claimed in claim 1, wherein $R_2$ and $R_3$ occupy the 2, 4 or 6 positions on the ring.

3. Mixtures of triaryl phosphates as claimed in claim 1, in which $R_5$ occupies the 6 position on the ring.

4. Mixtures of triaryl phosphates as claimed in claim 1 wherein at least one of $R_2$ and $R_3$ is isopropyl.

* * * * *